United States Patent [19]

Rushing

[11] 4,372,080

[45] Feb. 8, 1983

[54] TREATED PEANUT SEEDS

[75] Inventor: Kyle W. Rushing, Plano, Tex.

[73] Assignee: Gustafson, Inc., Dallas, Tex.

[21] Appl. No.: 244,765

[22] Filed: Mar. 17, 1981

Related U.S. Application Data

[63] Continuation-in-part of Ser. No. 111,726, Jan. 14, 1980, Pat. No. 4,339,456.

[51] Int. Cl.$^3$ .............................................. A01C 1/06
[52] U.S. Cl. .................................. 47/57.6; 424/274; 424/276; 424/330
[58] Field of Search ......................... 47/57.6, DIG. 9; 424/274, 276, 330

[56] References Cited

U.S. PATENT DOCUMENTS 3,728,099  4/1973  Chiles .................................. 47/57.6

*Primary Examiner*—Sam Rosen

*Attorney, Agent, or Firm*—Peterson, Palmatier, Sturm, Sjoquist & Baker, Ltd.

[57] ABSTRACT

A method of treating of peanut seeds with a fungicide effective against seed-borne pathogens consisting in treating the seeds with a suspension including oil as a base and also including active chemicals in the form of finely ground particles carried by the oil in the suspension and allowing the seeds to dry with the result that a coating including active chemicals remains on the seeds to minimize chemical dust related environmental and physical problems. The slurry contains a balance of non-phytotoxic mineral oil, water and solid materials providing the active ingredients, and emulsifiers. The seeds have a dried coating embracing and at least partially penetrating the testa of the seed and producing thorough contact with the entire periphery of the seed, the coating containing at least one fungicide effective against the seed-borne pathogens.

7 Claims, No Drawings

TREATED PEANUT SEEDS

This application is a continuation-in-part of my copending application Ser. No. 111,726, filed Jan. 14, 1980 now U.S. Pat. No. 4,339,456.

This invention relates to the treatment of peanut seeds and particularly the method of treating such peanut seeds.

BACKGROUND OF THE INVENTION

Peanut seeds are significantly different than other agronomic seeds and have presented some exceedingly difficult problems as relates to the application of pesticides or fungicides to the seed prior to planting.

The skin or testa of the seed is a very important and essential part of the peanut seed, but is fragile and subject to damage, depending upon the method and materials used in treating the seed.

The testa will be recognized as the thin and delicate membrane which embraces the peanut and oftentimes flakes off or is intentionally removed when peanuts are eaten. The testa provides the peanut embryo protection and also supplies essential nutrient enzymes to the germinating seed. The testa contains tannin, pectin and lipoids, and crystals of nitrogenous substance. Partial loss of the seed coat or testa reduces the likelihood that the peanut seed will germinate; and complete loss of the seed coat or testa makes it unlikely that there will be normal germination of the seed. Plants from seeds without the testa have significantly less vigor and produce significantly less yield than plants which grow from normal seeds with the skin or testa in place.

The susceptibility of seed coat damage and loss is dependent upon the type of the peanuts. Spanish and Bunch Type peanuts are more susceptible to damage than Runner Types.

The seed coat or testa also varies considerably in different types of peanuts. In the Spanish peanuts, which are some of the smaller peanuts grown in the United States, the seed coats or testa are relatively smooth and considerably smoother than the testa or seed coat of the Runner Types of peanuts which are generally somewhat larger or of an intermediate size as compared to the smaller Spanish peanuts. The largest peanuts are the Bunch Type peanuts, and these Bunch Type peanuts have seed coats which are considerably more wrinkled and less smooth than the testa of the Runner Type peanuts.

In order to minimize the likelihood of damage to the seed coat or testa during treating of peanut seeds, the seeds have been exclusively treated by applying a dry dust to the seed. Applying chemical treatments by a dust presents formidable problems in the application as well as in the handling of treated seeds prior to planting. The dust products have been finely ground or micronized so that it is very difficult to control the dust during application and handling. The recommended rates of usage of these dust products are 20 percent to 30 percent higher than the amount of chemical than the peanut seed can actually retain on its outside surface. The chemicals present in the dust have contact activity only, and as a result, this massive use of the dry chemicals on the peanut seeds does assure complete coverage and good chemical performance.

These chemical dusts used in treating peanuts are considered to be dust toxicants and are therefore the subject of intense interest by safety and governmental authorities. Many of the people who work with the peanut seeds have allergies responsive to the dust or skin conditions which are sensitive to the dust. Of course, the constant exposure to these dust conditions can present a very serious health hazard to the workers who must work with these peanut seeds. All of the people who handle or work with the seeds at various stages of treatment, handling and planting, including processors, truck drivers, dealers and farmers, are subject to these serious health hazards.

When it is considered that approximately 500,000 pounds of dust chemical seed protectants are required in order to adequately treat the amount of seed to plant the U.S. acreage, the excessive use of treatment by approximately 30 percent of this amount of dust chemical seed protectant is a sizable amount of chemical exposure for people involved in the peanut planting industry.

In a processing plant for treating peanut seeds, the actual treating area should have a dust-collecting system so as to remove the excessive dust from the treating area and ducting the dust outside. Clean air standards, established by both Federal and state and local governments require the air in both the treating area and the bagging area of a processing plant be treated and cleaned for minimum employee exposure. In order to fully comply, a totally enclosed air control system would be necessary at a projected cost of $50,000 to $100,000, depending upon the plant size. In view of the fact that the peanut seed processors operate on a very low gross profit margin, expenditures of this magnitude cannot be justified.

In addition, the chemical dust which is used for treating presents considerable problems to the seed processor in terms of applying the correct amount of the treating dust to the seed. Much of this seed treating is carried on in the southern states where high humidity is a frequent occurrence. High humidity causes the chemical dust to become sticky due to the fact that these dust products hydrate quite rapidly when exposed to high humidities. When the dust becomes sticky, measuring of the dust and causing of the dust to flow freely is extremely difficult and of course the amount applied to seeds becomes rather erratic.

When atmospheric conditions are extremely dry, then the problems of static electricity become extremely important in the handling of chemical dusts. Of course, static electricity also inhibits the flow of dust and the application of exact correct amounts to the seeds is extremely difficult.

Accordingly, unless the humidity conditions during processing is substantially exactly correct, flow problems are continually experienced in handling of dust.

The peanut grower who buys the treated seed is presented with varying problems by the problems of the processor. In many cases, the peanut seeds carry either an inadequate or excessive amount of dust. Inadequate amounts of treating dust on the seed result in a lower rate of germination of the seed in the field, and of course a reduced production. When the peanut seeds carry excessive amounts of chemical dust, the excessive amounts of dust present substantial problems to the grower in planting the seeds.

As indicated above, the chemical dusts become sticky under high humidity ambient conditions, which occur frequently during planting time for peanuts. The dust therefore causes the planting equipment to clog to the point of being inoperable or at least erratic in operation. The planter plates used to place individual seeds in the ground will clog to the point where the openings in the plates will not accept a seed so that the spacings between the seeds planted in the ground become non-uniform. Of course, such non-uniform plant spacing in the field will reduce the overall production of the field.

In the past, some attempts have been made to use slurry treatments with wettable powders and water to treat peanut seeds. These attempts provide quite unsuccessful, primarily because of the effect of the water on the very fragile seed coat or testa which, upon being wetted, becomes hydrated quite rapidly. Later, when the testa is permitted to dry, it shrinks substantially and flakes off the peanuts so as to substantially damage the peanut seed for planting purposes.

In the very distinctive seed coat or testa of the peanut seed, the rate of absorption of water or organic solvent products through the testa is quite rapid. The testa has several layers of cells, the outermost layer of cells being essentially empty. In the testa the second layer of cells contains the dense deposit of tannin, pectin, and lipoids; and the inner layer contains the crystals of nitrogenous substance, but not protein. When exposed to water, the testa acts as a sponge and the inflow of water is 20% to 56% greater than the outflow. Water tends to accumulate between the inner testa cell walls faster than the cotyledons can absorb it. This results in interference with normal germination in exclusion of oxygen and accumulation of carbon dioxide. Also, an exomosis of essential nutrients occurs.

The remaining seed with a partial seed coat or testa loss is referred to as a "Bull-Head"; and a peanut seed which has suffered complete seed coat loss is termed a "Bald-Head".

Because of the marked failure to adequately treat peanut seeds with the water based slurry, the treatment of seed by dusting has been the exclusive way of applying fungicides in recent years.

SUMMARY OF THE INVENTION

An object of the invention is to produce a method of treating peanut seeds which will eliminate health hazards to persons associated with processing, handling and planting such seed.

Another object of the invention is to produce a method of treating peanut seeds which will materially reduce the quantity of treatment applied to the seed, and thereby reduce the cost and hazards associated with obtaining necessary protection from the excess toxic dust during the treating of peanuts.

Another object of the invention is to produce for peanut seeds, a seed treatment which will be effective against principal pathogens and will eliminate health hazards to persons associated with processing, handling, testing, and planting such seed.

A principal feature of the invention is the application of the treatment chemical to peanut seeds in the form of an oil based slurry or colloidal suspension, and wherein the active ingredients or particles in the suspension are exceedingly small.

Another principal feature of the invention is a method of treating peanut seeds through the use of an oil base carrier containing finely ground particles of active ingredients which uniformly cover the peanut seed to provide thorough protection.

Still another feature of the invention is the method of treating peanut seeds by utilizing a liquid as a carrier for the active ingredients and wherein the liquid has an oil base.

Another principal feature of the invention is a seed treatment for peanut seeds which is dustless and which is a slurry or colloidal suspension containing a balance of non-phytotoxic mineral oil, water, and solid materials providing the active ingredients. It has been found that the peanut seed can tolerate a balance ratio of oil to water in the slurry. The range of oil should be twenty five to forty five percent (25-45%) by weight in the slurry; and the water concentration cannot exceed thirty eight percent (38%) by weight of the slurry.

A principal advantage of the present invention is the elimination of toxic dust on peanut seeds and the elimination of related dust problems at application and bagging stations in a processing plant and at other locations of seed handling, trucking and planting. The dust on the seeds is essentially eliminated as to minimize environmental and physical problems related to processing, handling and planting the seeds which have previously been caused by the effect of humidity and static electricity and the extreme toxic nature of these chemical dusts.

Another principal advantage of the invention is the uniform application of treatment material to peanut seeds so as to thoroughly protect the seeds, but without using excessive amounts of the treatment material.

Still another advantage of the invention is the uniform coating of peanut seeds with non-dusting seed treatment which will not interfere with germination and sprouting of the seed but which will protect the seed against seed-borne pathogens, with an overall efficacy at least as equal to the prior art dust treatments.

A significant advantage obtained by the present invention is, in addition to obtaining treatment of peanut seeds which efficacy at least as good as with prior treatments, the elimination of dust associated with prior peanut seed treatments, and the elimination of surface residues on the treated seeds; further providing immediate drying of peanut seeds during treating to eliminate the need for special handling or drying of the seeds after treating.

In addition to the elimination of health hazards, the overriding advantages obtained by the present invention are that the treating is accomplished with an oil base slurry which is not affected at all by humidity, and therefore the high humidity problems of sticking of the dust are eliminated, and the low humidity problems related to static electricity are also eliminated; and further, the clogging of the growers planting machinery is essentially eliminated as a result of treating the seeds according to the present invention. Also the processor will be able to apply uniform and carefully controlled amounts of treating material to the seeds so that the peanuts received by the grower will be of standard quality, all being treated with the proper amount of the treating material. Such treating material or active ingredients may be varied according to the needs of local growing conditions.

DETAILED SPECIFICATION

The usual purpose of treating peanut seeds is to control and effectively eliminate the fungi and bacteria on the peanut seeds to be planted.

Some of the more important seed-borne pathogens that must be controlled include *Aspergillus niger, Aspergillus flavus-oryzae,* Bacteria, *Penicillium spp.,* Rhizopus arrhizus, and *Trichoderma spp.* Other fungi which need to be controlled in certain situations include *Alternaria sp., Chetomium sp., Curvularia sp., Fusarium oxysporum, Fusarium roseum, Fusarium solani, Mucor sp., Mucor*

*haemalis, Rhizoctonia solani,* Sterile fungi, *Thielavia terricola,* and *Zygorhynchus sp.* A number of different active chemical products are useful in controlling the seed-borne pathogens related to peanut seed. Since these products are contact fungicides, the dust formulations used are applied at excessive rates to permit total seed coverage. The non-retained excess toxic dust relates to the environmental and physical problems in the peanut seed industry.

The present invention deals principally with the manner of application of active chemical ingredients serving as pesticides to the peanuts.

According to the present invention, peanut seeds are treated by mixing the active ingredients or treating chemicals into a homogeneous oil based slurry or suspension which is then applied to the peanut seeds. The peanut seeds are actually thoroughly covered with the oil based suspension carrying the treating chemicals with the result that a homogeneous coating including the treating chemicals remain on the seed. The suspension may be applied to the seeds in any of a number of ways, but is preferably applied by producing a mist of the suspension, and then passing the seed through the air-borne mist as by gravity. The treating chemicals are in the form of finely ground particles which adhere to the peanut seed treated by the slurry and contained in the homogeneous coating which remains on the seeds. The slurry which is applied to the peanut seeds migrates around the entire periphery of each of the peanut seeds so that the coating covers the entire outer periphery of the seeds. In the process of applying the slurry, all of the outer surface of the testa or seed coat including all of the wrinkles or irregularities is coated with the oil based slurry or suspension.

Surprisingly, it has been found that after applying the liquid treatment, the peanut seeds are completely dry in six to ten minutes, and there is no residue remaining on the outer surface. Regardless of whether the treated seeds are put into bags of any type, are put through a dryer or laid out in the air, the seeds are dry within six to ten minutes. This permits the seed processor to immediately bag the peanut seeds after treatment, although at that time the seeds are visibly wet and are wet to the touch so that a person's hand may be stained to handle them. The bags may be paper, film or cloth and may be immediately put into storage or shipped to customers.

An important aspect to the present invention is the balance of the non-phytotoxic mineral oil, and water and solid materials including the active ingredients in the slurry. The key to the balance is related to the proportion of oil in the slurry. If the proportion of oil is too low, the water will adversely affect the skin or testa; and if the proportion of oil is too high, the oil will seal the outer surface area of the testa and will seal the porous openings, not permitting oxygen, carbon dioxide, and water osmatic transfer. The oil should be between twenty five and forty five percent (25–45%) by weight of the slurry. The water concentration cannot exceed thirty eight percent (38%) by weight of the slurry; but the proportion of water may be less, or in the range of twenty five and thirty eight percent (25–38%) by weight of the slurry. A small quantity of emulsifier is also added to the slurry. No additional quantities of water may be added to the slurry; and the only water in the treatment to be used is that originally contained.

Of course, small quantities of dye should be added; and small proportions of spreader material is preferably added to cause the slurry to uniformly spread over the surface of the testa of the peanut seeds. A typical spreader material is known as Triton B 1956, sold by Rohm & Hass Chemical Co., Independence Mall West, Philadelphia, PA 19105.

Recognizing that different active ingredients may be necessary to combat dominant pathogens in various geographical growing locations, the various flowable treatment chemicals may be added or omitted according to need. The proportion of the oil base carrier may be decreased or increased to maintain the overall oil to water ratio in the slurry. The carrier is compatible with the various fungicidal chemicals useful in treating peanut seeds, such as flowable Botran 30C, Captan 30DD, Vitavax 30C, and Gustafson 42-S (a flowable Thiram). All such flowable treating chemicals contain water, emulsifiers and oils. The dyes included are typically on the order of Rhodamine dye.

It has been found satisfactory to use a refined and distilled mineral oil as the oil base of the slurry.

The treating chemicals known as Captan, Botran and Vitavax have been found to be effective in treating peanut seeds, as against the principal seed-borne pathogens. Botran is a registered trademark of the Upjohn Company, Kalamazoo, Michigan; and Vitavax is a registered trademark of Uniroyal Chemical, a division of Uniroyal, Inc. of Naugatuck, Connecticut. These chemicals are initially in the form of a dry dust, and are formulated into a colloidal suspension with oil. These formulated chemical products all contain approximately three pounds of active dry dust per gallon of product, and are all formulated under the same formulation technology at Gustafson Chemicals, Inc., Marcene, Idaho.

It has been found that approximately twelve to sixteen fluid ounces of the treatment-carrying oil slurry per hundred weight of peanut seeds treated is satisfactory to give adequate coverage.

Several different chemicals and combinations have been used as seed treatments in the suspension to produce the coating for the peanuts. After the suspension is applied to the peanut seeds, as to produce a coating on the peanut seeds, the seeds are allowed to dry. The end product of this treatment is the peanut seed with a dried coating embracing and thoroughly covering the testa. The coating extends into the wrinkles of the testa and at least partially penetrates the testa. The coating contains at least one contact type fungicide, as described, effective against seed-borne pathogens.

EXAMPLE 1

Captan 30-DD flowable has been used as a seed treatment, utilizing 3.0 fluid ounces of the seed treatment per hundred weight of peanut seeds. The Captan was mixed into an oil base slurry, adding oil sufficient to apply 6.0 fluid ounces of the total slurry including the Captan, per hundred weight of seeds treated. The oil used as a base for the slurry is a mineral oil, refined and distilled from crude. Typical of the oil used is an oil produced by Witco Chemical Company of Bakersfield, California, identified as Product 9093LM with a specific gravity at 60° F. of 0.8751 and a flash point, COC of 320° F.

TABLE 1

COLONIES OF FUNGI AND BACTERIA FROM 200 SEED.

| Seed Borne Pathogens | NONTREATED CONTROL | GUSTAFSON CAPTAN[1] 30 DD FLOWABLE AT 3.0 FL OZ/CWT | TERRA-COAT L-205[2] AT 4.0 FL OZ/CWT | (DUST) DIFOLATAN BOTRAN (60-20) 5.0 OZ/CWT |
|---|---|---|---|---|
| *Aspergillus niger* | 161 | 0 | 111 | 1 |
| *Aspergillus flavus-oryzae* | 81 | 0 | 57 | 1 |
| Bacteria | 17 | 0 | 47 | 8 |
| Penicillium spp. | 42 | 0 | 92 | 1 |
| *Rhizopus arrhizus* | 20 | 4 | 0 | 2 |
| Trichoderma spp. | 4 | 0 | 5 | 1 |
| Other fungi[a] | 6 | 0 | 6 | 1 |
| Total | 331 | 4 | 318 | 15 |

[a] Includes Alternaria sp., Chetomium sp., Curvularia sp., *Fusarium oxysporum, F. roseum, F. solani*, Mucor sp., Rhizoctonia solani, sterile fungi, *Thielavia terricola*, and Zygorhynchus sp.
[1] applied in slurry @ 6.0 fl oz/cwt
[2] applied at recommended rate

TABLE 2

GERMINATION OF FLOWABLE PEANUT TREATMENTS APPLIED COMMERCIALLY COMPARED TO THE STANDARD DUST TREATMENT AND THE NONTREATED CHECK.

| TREATMENTS | FORMULATED RATE/CWT | NORMAL | ABNORMAL DISEASED | OTHER | DEAD |
|---|---|---|---|---|---|
| Nontreated Control | — | 5.0 | 22.5 | 0.0 | 72.5 |
| Gustafson Captan 30 DD Flowable | 3.0 fl oz | 52.6 | 17.7 | 5.1 | 24.6 |
| Terra Coat L-205 | 4.0 fl oz | 12.7 | 28.7 | 1.3 | 57.3 |
| Difolatan-Botran (60-20)-DUST | 5.0 oz. | 84.0 | 10.0 | 5.0 | 1.0 |

There are a number of other similar oils available which would also be suitable, all mineral oils refined and distilled from crude, such as Shell 68-S oil product code 86625 produced at Shell Refinery, Martinez, California, with a flash point of 320°; Sun Oil Product 8070 Neutral, product code KM133-714 with a flash point of 350° to 360° F., sold by Kerr-McGee Refining Corporation of Oklahoma City, Oklahoma; or other Kerr-McGee products identified as product name 8070 E-2 with a product code KM133-998, or product name 8070 E-1 with a product code KM 133-996, both with flash points of approximately 350 to 360° F.

In this example, the Terra Coat L-205 seed treatment was used in a concentrate of 4.0 fluid ounces per hundred weight of peanut seeds treated, and also mixed into an oil based slurry, wherein six fluid ounces of the slurry including the Terra Coat L-205 was applied per hundred weight of seed treated.

The fungicide treated seed and controls were plated ten per Petri dish and were incubated in the dark for seven days after which the colonies of fungi and bacteria were enumerated; with the exception of the enumeration of the Rhizopus and Trichoderma colonies which were enumerated after three days because these grow so rapidly.

The effectiveness of the chemical treatment of the seed is found in Table 1 which compares to the nontreated control seeds, and the seeds treated with the standard Difolatan-Botran (60-20).

Also as a part of this example, laboratory germination tests were made of the seeds which were treated with the oil based slurry seed treatment and compared against non-treated seeds and seeds treated with the standard dust control treatment of Difolatan and Botran (60-20). The germination checks are reported in Table 2.

Treatment of the seeds in this example was effective and the oil based slurry did not cause damage to the seeds. Although the actual chemical treatments used were lacking in some respects, the Captan 30-DD seed treatment alone with the oil based slurry produced outstanding performance based on the expectancies of this Captan seed treatment.

EXAMPLE 2

In this example, numerous seed treatment chemicals were applied alone in an oil based slurry and various mixtures of chemical seed treatment were applied in an oil based slurry, each being applied to one hundred peanut seeds of the Florunner variety and another one hundred of Florigiant variety.

Although the various chemical treatments used in the oil based slurries had varying efficacy as relates to the seed-borne pathogens counted, the coatings produced on the seeds by the treating slurries did not produce Bull-heads or Bald-heads. In each of the seed treatments, nine fluid ounces of the total slurry, including the active ingredients, was used per hundred weight of seeds being treated. Table 3 and Table 4 show the actual fluid ounces of the treating chemical used in the slurry. The oils used were again mineral oils refined and distilled from crude, as explained in Example 1.

The Treatment No. 7 indicated in Tables 3 and 4 is the standard Difolatan-Botran (60-20) dust which is the standard used in the industry prior to this time. Tables 3 and 4 indicate the colonies of fungi and bacteria of various identifications counted on the plated seeds.

As a part of this example, a number of the Florunner peanut seeds treated with varying seed treatments applied with the oil slurry were laboratory germinated in comparison with non-treated control seeds and seeds treated with the standard dust treatment of Difolatan-Botran (60-20).

TABLE 3

COLONIES FUNGI AND BACTERIA FROM 100 FLORUNNER PEANUT SEED

| Seed Borne Pathogens | TREATMENT NO.[a][b] | | | | | | |
|---|---|---|---|---|---|---|---|
| | 1 | 2 | 3 | 4 | 5 | 6 | 7 |
| *Aspergillus flavus* | 23 | 9 | 21 | 9 | 10 | 5 | 2 |
| *Aspergillus niger* | 81 | 6 | 11 | 47 | 2 | 1 | 2 |
| *Aspergillus repens* | 57 | 3 | 14 | 8 | 2 | 1 | 0 |
| Bacteria | 2 | 5 | 9 | 1 | 4 | 0 | 7 |
| Penicillium spp. | 40 | 13 | 35 | 32 | 11 | 8 | 3 |
| *Rhizopus arrhizus* | 18 | 8 | 6 | 10 | 3 | 1 | 2 |
| Trichoderma spp. | 4 | 3 | 9 | 9 | 1 | 0 | 1 |
| Other fungi | 1 | 1 | 3 | 1 | 1 | 2 | 0 |
| TOTAL | 226 | 48 | 108 | 117 | 34 | 16 | 17 |

[a]1. Nontreated Control
2. Captan 30 DD @ 3.0
3. Botran 30 Fl. @ 3.0
4. Vitavax 30 C @ 3.0
5. Captan 30 DD + Botran 30 F @ 3.0 + 3.0
6. Captan 30 DD + Botran 30 F + Vitavax 30 C @ 3.0 + 3.0 + 3.0
7. Difolatan-Botran (60-20) Dust @ 5.0 oz.
[b]All Flowables applied in slurry @ 9.0 fl oz total slurry/cwt

TABLE 4

COLONIES OF FUNGI AND BACTERIA FROM 100 FLORIGIANT PEANUT SEED

| Seed Borne Pathogens | Treatment No.[a][b] | | | | | | |
|---|---|---|---|---|---|---|---|
| | 1 | 2 | 3 | 4 | 5 | 6 | 7 |
| *Aspergillus flavus* | 56 | 12 | 42 | 27 | 17 | 13 | 4 |
| *Aspergillus niger* | 73 | 20 | 26 | 62 | 12 | 5 | 0 |
| Bacteria | 54 | 26 | 35 | 47 | 55 | 16 | 20 |
| Penicillium spp. | 55 | 3 | 20 | 89 | 11 | 1 | 1 |
| *Rhizopus arrhizus* | 70 | 20 | 72 | 75 | 24 | 21 | 14 |
| Trichoderma spp. | 1 | 0 | 7 | 9 | 4 | 0 | 3 |
| Other fungi | 0 | 4 | 0 | 1 | 0 | 0 | 0 |
| TOTAL | 309 | 85 | 202 | 260 | 123 | 56 | 42 |

[a]1. Nontreated Control
2. Captan 30 DD @ 3.0
3. Botran 30 Fl @ 3.0
4. Vitavax 30 C @ 3.0
5. Captan 30 DD + Botran 30 F @ 3.0 + 3.0
6. Captan 30 DD + Botran 30 F + Vitavax 30 C @ 3.0 + 3.0 + 3.0
7. Difolatan-Botran (60-20) Dust @ 5.0 oz.
[b]All Flowables applied in slurry @ 9.0 fl.oz. total slurry/cwt Germination of these seeds treated with various treatments applied with the oil slurry is reported in Table 5. It will be recognized that the number of seeds germinated is closely comparable between the seeds treated with the standard dust treatment and certain of the seeds to which treatment is applied with the oil based slurry.

EXAMPLE 3

In Example 3, the results of which are found in Tables 6 and 7, additional quantities of one hundred Florunner peanut seeds were again treated with the flowable Captan 30-DD and the flowable Botran 30 in an oil based slurry, and the second seed treatment also included the flowable Vitavax. The oils used were as explained in Example 1. The total slurry including the active ingredients was applied at a rate of nine fluid ounces per hundred weight of seeds treated. Again, the colonies of fungi and bacteria were counted, and germination tests were performed, and the results were quite favorably comparable to the results obtained with the dust chemical treatment provided by the Botec standard dust treatment. The treatment with the oil based slurry and chemical treatments carried thereby caused no Bull-heads or Bald-heads in the peanuts treated.

EXAMPLE 4

In Example 4, numerous concentrations of Captan and Botran flowable are demonstrated in comparison with the non-treated control peanut seeds and the peanut seeds treated with the standard dust treatment of Difolatan-Botran (60-20). All of the flowables were applied in a slurry with fourteen fluid ounces total slurry per hundred weight of peanut seeds treated. Several of the treatments with different combinations of active ingredients produced results vary comparable to those produced with the standard dust treatment.

TABLE 5

SUMMARY OF STANDARD GERMINATIONS ON FLORUNNER PEANUTS OF VARIOUS FLOWABLE PEANUT SEED TREATMENTS AS COMPARED TO A STANDARD DUST PRODUCT AND NONTREATED CONTROL

| | NORMAL | DISEASED | ABNORMAL | DEAD |
|---|---|---|---|---|
| Nontreated Control | 27 | 63 | 33 | 40 |
| Captan 30 DD | 69 | 9 | 25 | 6 |
| Botran 30 Flowable | 68 | 24 | 25 | 7 |
| Vitavax 30 C | 62 | 23 | 31 | 7 |
| Captan 30 DD + Botran 30 Fl | 75 | 3 | 20 | 5 |
| Captan 30 DD + Botran 30 Fl + Vitavax 30 C | 82 | 3 | 18 | 4 |
| Difolatan-Botran (60-20) @ 5.0 | 81 | 0 | 16 | 3 |

[1]All Flowables applied in slurry @ 9.0 fl oz total slurry/cwt

TABLE 6

COLONIES OF FUNGI AND BACTERIA FROM 100 FLORUNNER PEANUT SEED COMMERCIALLY TREATED COMPARISONS OF FLOWABLE SEED TREATMENTS (9 OZ. TOTAL SLURRY/CWT) TO THE STANDARD BOTEC TREATMENT AND THE NONTREATED CHECK

| | NUMBER OF COLONIES OF FUNGI AND BACTERIA TREATMENT AND RATE | | | |
|---|---|---|---|---|
| Seed-Borne Pathogens | NONTREATED CONTROL | CAPTAN 30 DD BOTRAN 30 FL @ 3.0 + 3.0 | CAPTAN 30 DD + BOTRAN 30 FL + Vitavax 30 C 3.0 + 3.0 + 3.0 | BOTEC (DUST) |
| *Aspergillus flavus* | 33 | 4 | 1 | 0 |
| *Aspergillus niger* | 83 | 5 | 5 | 10 |
| Bacteria spp. | 0 | 10 | 23 | 0 |
| *Mucor haemalis* | 3 | 0 | 0 | 0 |
| *Fusarium roseum* | 0 | 3 | 3 | 0 |
| Penicillium spp. | 57 | 3 | 3 | 0 |
| *Rhizopus arrhizus* | 8 | 0 | 1 | 2 |

TABLE 6-continued
COLONIES OF FUNGI AND BACTERIA FROM 100 FLORUNNER PEANUT SEED COMMERCIALLY TREATED COMPARISONS OF FLOWABLE SEED TREATMENTS (9 OZ. TOTAL SLURRY/CWT) TO THE STANDARD BOTEC TREATMENT AND THE NONTREATED CHECK

| | NUMBER OF COLONIES OF FUNGI AND BACTERIA TREATMENT AND RATE | | | |
|---|---|---|---|---|
| Seed-Borne Pathogens | NONTREATED CONTROL | CAPTAN 30 DD BOTRAN 30 FL @ 3.0 + 3.0 | CAPTAN 30 DD + BOTRAN 30 FL + Vitavax 30 C 3.0 + 3.0 + 3.0 | BOTEC (DUST) |
| Trichoderma spp. | 5 | 6 | 0 | 1 |
| Total Colonies | 189 | 35 | 36 | 13 |

TABLE 7
SUMMARY OF STANDARD GERMINATIONS OF FOUNDATION FLORUNNER PEANUTS COMMERCIALLY TREATED

| TREATMENTS | NORMAL | ABNORMAL DISEASED | OTHER | DORM. | DEAD |
|---|---|---|---|---|---|
| Non-treated Check | 31.0 | 64.0 | 0.0 | 1.0 | 4.0 |
| Botec @ 5.0 oz | 84.0 | 1.0 | 5.0 | 10.0 | 0.0 |
| Gustafson Captan 30 DD + Botran 30 Fl. @ 3.0 + 3.0 fl oz | 86.0 | 4.0 | 2.0 | 8.0 | 0.0 |
| Gustafson Captan 30 DD + Botran 30 Fl + Vitavax 30C @ 3.0 + 3.0 + 3.0 fl oz | 84.0 | 3.0 | 1.0 | 12.0 | 0.0 |

TABLE 9
FIELD EMERGENCE OF FOUNDATION FLORUNNER PEANUT SEED NEW FLOWABLE SEED TREATMENTS vs. STANDARD BOTEC DUST TREATMENT

| TREATMENTS* | PLANTS EMERGED[1] | ACRE POPULATION |
|---|---|---|
| 1. CAPTAN 30-DD + BOTRAN 30 Fl @ 3.0 + 3.0 | 55.38 | 55,375 |
| 2. CAPTAN 30-DD + BOTRAN 30 Fl + VITAVAX-30C @ 3.0 + 3.0 + 3.0 | 52.94 | 52,940 |
| 3. BOTEC (Std.) @ 5.0 | 47.07 | 47,065 |

*Applied @ total slurry of 14.0 fl. oz.
[1]16 Replications × 13.25 feet

TABLE 10
PEANUT SEED PATHOGEN ISOLATIONS FROM PEANUT SEED-TAMNUT 74 VARIETY-TREATED WITH VARIOUS CHEMICAL FORMULATIONS. JULY 1979. COASTAL PLAINS EXP. STATION, TIFTON, GEORGIA.

| | Number of Colonies Found[2] Treatments Evaluated[1] | | | | |
|---|---|---|---|---|---|
| Disease Pathogens | I | II | III | IV | V |
| Aspergillus niger | 15 | 1 | 0 | 1 | 1 |
| Aspergillus flavus | 29 | 2 | 2 | 1 | 0 |
| Bacteria spp. | 0 | 0 | 5 | 6 | 6 |
| Penicillium spp. | 100 | 20 | 9 | 9 | 1 |
| Rhizopus arrhizus | 26 | 3 | 8 | 3 | 11 |
| Fusarium roseum | 0 | 0 | 0 | 0 | 0 |
| Alterneria spp. | 0 | 0 | 0 | 0 | 0 |
| TOTAL | 170 | 26 | 24 | 20 | 19 |

[1]I. Untreated
II. Captan 30 DD + Botran 30 F + Gustafson S.P. Extender @ 3.0 + 3.0 + 2.0
III. Captan 30 DD + Botran 30 F + Gustafson S.P. Extender @ 3.0 + 3.0 + 4.0
IV. Captan 30 DD + Botran 30 F + Gustafson S.P. Extender @ 3.0 + 3.0 + 6.0
V. Vitavax 300 (Dust) @ 5.0
[2]Number of colonies isolated from a total of 100 seed.

TABLE 11
PEANUT SEED PATHOGEN ISOLATIONS FROM PEANUT SEED-FLORUNNER VARIETY-TREATED WITH VARIOUS CHEMICAL FORMULATIONS. JULY 1979. COASTAL PLAINS EXP. STATION, TIFTON, GEORGIA

| | Number of Colonies Found[2] Treatments Evaluated[1] | | | | |
|---|---|---|---|---|---|
| Disease Pathogens | I | II | III | IV | V |
| Aspergillus niger | 62 | 8 | 2 | 6 | 0 |
| Aspergillus flavus | 76 | 8 | 8 | 6 | 0 |
| Bacteria spp. | 0 | 2 | 2 | 4 | 0 |
| Penicillium spp. | 0 | 5 | 2 | 5 | 0 |
| Rhizopus arrhizus | 71 | 6 | 5 | 6 | 77 |
| Fusarium roseum | 0 | 1 | 0 | 0 | 2 |
| Alterneria spp. | 0 | 2 | 0 | 0 | 0 |
| TOTAL | 209 | 32 | 19 | 27 | 79 |

[1]I. Untreated
II. Captan 30 DD + Botran 30 F + Gustafson S.P. Extender @ 3.0 + 3.0 + 2.0
III. Captan 30 DD + Botran 30 F + Gustafson S.P. Extender @ 3.0 + 3.0 + 4.0
IV. Captan 30 DD + Botran 30 F + Gustafson S.P. Extender @ 3.0 + 3.0 + 6.0
V. Difolatan-Botran (60-20) @ 5.0
[2]Number of colonies isolated from a total of 100 seed.

The same (60-20) dust according to Table 11. The effectiveness of the treatment will be recognized in the rates of treatment applied. Application of 14 or 16 ozs. per hundred weight will also produce effective protection. The oil based extender uses the same type of oil specified in Example 1.

EXAMPLE 6

Field emergence of peanut seeds to which 12 oz. of seed treatment per hundred weight of seeds treated, is seen to be very satisfactory according to Table 12. The oil used in the slurry or suspension is the same type as indicated in Example 1.

EXAMPLE 7

The effects of applying peanut seed treatments at rates of twelve and fourteen ounces of treatment per hundred weight of peanut seed as relates to elimination fungicide colonies on the seeds and as relates to rate of germination, are evident in Tables 13 and 14. These are compared with the percentages of clean seed and germination of peanut seeds treated with the standard Difolatan-Botran (60-20) dust, and of untreated seeds. The effectiveness of the treatment applied as an oil based suspension or slurry is clear. The oils used in the treatment is of the same type as described in Example 1.

A study was made of the compatibility of the flowable peanut seed treatments according to the present invention.

EXAMPLE 8

First, the pH levels of the components of the treatment slurry were determined. These are set forth in Table 15. The Gustafson Peanut Binder is the same as the Gustafson S.P. Extender mentioned in Tables 11–14, and includes mineral oil, water and emulsifiers. The Gustafson Peanut Slurry Additive is a material to induce dispersion of the components of the slurry thorough spreading of the treatment slurry over the entire surface of the testa of the peanut seed and is Triton B 1956. The Gustafson Peanut Dye is Rhodamine dye. The Gustafson 42-S is flowable Thiram. The other active ingredients, Botran 30C and Vitavax 30C are also flowable. The flowable active ingredients all include water, oil and emulsifiers. The same components are found in the following examples:

TABLE 12

EVALUATION OF VARIOUS FUNGICIDE SEED TREATMENTS IN COMBINATION WITH GUSTAFSON'S S.P. EXTENDER AS TO THE EFFECT ON FIELD EMERGENCE. AUGUST 15, 1979. PILOT POINT, TX.

| | | Varieties[1] | | | |
|---|---|---|---|---|---|
| | | Tamnut 74 | | Florunner | |
| | | % Emergence-Days Post-Planting | | | |
| Treatment | Form. Rate | 8 Days | 15 Days | 8 Days | 15 Days |
| Untreated Check | — | 52.0 | 68.0 | 21.6 | 49.6 |
| Captan 30-DD + Botran 30F | 3.0 + 3.0 | 64.0 | 80.0 | 36.0 | 80.8 |
| Captan 30-DD + Botran 30F + Gustafson S.P. Extender | 3.0 + 3.0 + 6.0 | 66.4 | 88.8 | 44.8 | 82.4 |
| Difolatan-Botran (60-20)-Dust | 5.0 | 66.4 | 85.6 | 44.0 | 71.2 |

[1] 12 fl. oz. slurry/cwt seed

TABLE 13

LABORATORY GERMINATION OF VARIOUS FUNGICIDE SEED TREATMENTS IN COMBINATION WITH GUSTAFSON'S S.P. EXTENDER AS TO EFFECT ON TOTAL GERMINATION. AUBURN UNIVERSITY, AUBURN, ALABAMA. OCTOBER 1979

| | | Tamnut 74[1] | |
|---|---|---|---|
| Treatment | Form. Rate | % Clean Seed | % Germination |
| Untreated Check | — | 46.0 | 80.0 |
| Captan 30-DD + Botran 30 F + Gustafson S.P. Extender | 4.0 + 4.0 + 4.0 | 90.5 | 90.5 |
| Captan 30-DD + Botran 30 F + Vitavax 30 C + Gustafson S.P. Extender | 4.0 + 4.0 + 3.0 + 1.0 | 87.0 | 87.0 |
| Difolatan-Botran (60-20) | 5.0 | 84.0 | 84.5 |

[1] Total slurry of 12.0 fl.oz./cwt

TABLE 14

LABORATORY GERMINATION OF VARIOUS FUNGICIDE SEED TREATMENTS IN COMBINATION WITH GUSTAFSON'S S.P. EXTENDER AS TO THE EFFECT ON TOTAL GERMINATION. AUBURN UNIVERSITY, AUBURN, ALABAMA. OCTOBER 1979

| | | Florunner[1] | |
|---|---|---|---|
| Treatment | Form. Rate | % Clean Seed | % Germination |
| Untreated Check | — | 4.0 | 72.0 |
| Captan 30-DD + Botran 30 F + Gustafson S.P. Extender | 4.0 + 4.0 + 6.0 | 91.0 | 91.0 |
| Captan 30-DD + Botran 30 F + Vitavax 30 C + Gustafson S.P. Extender | 4.0 + 4.0 + 3.0 + 4.0 | 86.0 | 86.0 |
| Difolatan-Botran (60-20) | 5.0 | 84.8 | 85.0 |

[1] 14 fl.oz. slurry/cwt

TABLE 15

| | pH. level |
|---|---|
| Gustafson 42-S | 7.30 |
| Botran 30 C | 7.60 |
| Vitavax 30 C | 7.60 |
| Gustafson Peanut Binder | 7.60 |
| Gustafson Peanut Slurry Additive | 7.20 |
| Gustafson Peanut Red Dye | 2.60 |

EXAMPLE 9

The compatibility of a Product II in two different application rates are reported in Tables 16 and 17. The Sample 1 is for Spanish and Valencia Peanut Types; and the Sample 2 is for Runner and Virginia Peanut Types.

TABLE 16

| | PRODUCT II | | | |
|---|---|---|---|---|
| | Sample 1** | | Sample 2*** | |
| | % V/V | Use Rate | % V/V | Use Rate |
| Gustafson 42-S | 24.71 | 3.00 | 19.820 | 3.00 |
| Botran 30 C | 24.71 | 3.00 | 19.820 | 3.00 |
| Gustafson Peanut Binder | 49.42 | 6.00 | 59.450 | 9.00 |
| Gustafson Peanut Slurry Additive | .58 | .07 | .455 | .07 |
| Gustafson Peanut Dye | .58 | .07 | .455 | .07 |
| Total Suspension: | 100.00% | 12.14 fl.oz. | 100.00% | 15.14 fl.oz. |

TABLE 17

Product Description: Fungicide Suspension - Product II
Compatibility Procedure: Products as identified under Product II were measured and uniformly mixed together to form a 500 ml. homogeneous test suspension. The samples evaluated for initial physical compatibility and then placed on vibration-free surface at 20–30° C. Samples allowed to stand 24 hours under these conditions without being disturbed at which time samples were again evaluated.

Results:

| | Sample 1 | | Sample 2 | |
|---|---|---|---|---|
| | Initial | 24 Hours | Initial | 24 Hours |
| pH | 4.95 | 5.0 | 4.95 | 5.0 |
| Agglomerates | None | None | None | None |
| Separation | None | None | None | None |
| Settling Out | None | None | None | None |
| Viscosity | Acceptable | Acceptable | Acceptable | Acceptable |
| Dispersion | Good | * | Good | * |
| Spontaneity | Poor-Fair | * | Poor-Fair | * |
| Tendency to Jell | None | None | None | None |

* Not Applicable
Conclusions: Acceptable pysicial compatibility for commercialization

EXAMPLE 10

The compatibility of a Product III in two different application rates are reported in Tables 18 and 19. The Sample 1 is for Spanish and Valencia Peanut Types; and the Sample 2 is for Runner and Virginia Peanut Types.

TABLE 18

| | Product III | | | |
|---|---|---|---|---|
| | Sample 1 | | Sample 2 | |
| | % V/V | Use Rate | % V/V | Use Rate |
| Gustafson 42-S | 24.71 | 3.00 | 19.820 | 3.00 |
| Botran 30C | 24.71 | 3.00 | 19.820 | 3.00 |
| Vitavax 30C | 24.71 | 3.00 | 19.820 | 3.00 |
| Gustafson Peanut Binder 62% oil, water, emulsifier | 24.71 | 3.00 | 39.640 | 6.00 |
| Gustafson Peanut Slurry Additive | .58 | .07 | .455 | .07 |
| Gustafson Peanut Dye | .58 | .07 | .455 | .07 |
| Total Suspension | 100.00% | 12.14 fl. oz. | 100.00% | 15.14 fl. oz. |

TABLE 19

Product Description: Fungicide Suspension - Product III
Compatibility Procedure: Same as in Table 17

Results:

| | Sample 1 | | Sample 2 | |
|---|---|---|---|---|
| | Initial | 24 Hours | Initial | 24 Hours |
| pH | 5.05 | 5.10 | 5.0 | 5.05 |
| Agglomerates | None | None | None | None |
| Separation | None | None | None | None |
| Settling Out | None | None | None | None |
| Viscosity | Acceptable | Acceptable | Acceptable | Acceptable |
| Dispersion | Good | * | Good | * |
| Spontaneity | Poor-Fair | * | Poor-Fair | * |
| Tendency to Jell | None | None | None | None |

*Not applicable
Conclusions:
Acceptable physical compatibility for commercialization.

In another series of Examples 11–14, Peanut Treatments II and III, which are the same as Products II and III respectively as in Examples 9 and 10, at different application rates were planted and/or germinated in field and laboratory with excellent results. The Examples define the components of the Treatments, and set forth the percentage by weight of the overall amounts of oil; solids (active ingredients); water; dyes and additives in the respective Treatments. The fluid ounce contents of the various components per cwt of peanut seed of the Treatments II and III are set forth in Table 20.

TABLE 20

Flowable Peanut Treatment II

Gustafson 42-S + Botran 30C + Gustafson Peanut Binder + Gustafson Slurry Additive + Gustafson Peanut Dye
Example 13. Spanish & Valencia - 3.0 + 3.0 + 6.0 + 2.0cc + 2.0cc
Example 11. Runner & Bunch - 3.0 + 3.0_9.0 + 2.0cc + 2.0cc Flowable Peanut Treatment III Gustafson 42-S + Botran 30C + Vitavax 30C + Gustafson Peanut Binder + Gustafson Slurry Additive + Gustafson Peanut Dye
Example 14. Spanish & Valencia = 3.0 + 3.0 + 3.0 + 3.0 + 2.0cc + 2.0cc
Example 12. Runner & Bunch - 3.0 + 3.0 + 3.0 + 6.0 + 2.0cc + 2.0cc

EXAMPLE 11

BUNCH & RUNNER TYPE PEANUTS

A Treatment II slurry suspension (oil based) was prepared of this invention by blending together 3.0 fl. oz. of 42-S (Thiram); 3.0 fl. oz. of Botran 30C; 9.0 fl. oz. of Gustafson Peanut Binder; 2.0 cc of Rhodamine dye; 2.0 cc of Triton B-1956. This suspension was blended together to make a homogeneous mixture and was applied to the peanut seed at the rate of 4.4 cc per pound. On the standard germination test, the % germination was equivalent to the dust standard. Upon laboratory investigation, the % disease control was also comparable. Some 40,000 pounds of seed were commercially treated and 400 acres planted. Field performance was excellent with no planter-plate problems reported, i.e. no accumulation of treatment on the planter parts. Upon storing these treated seeds for six months, no increase in loss of seed coat (Testa) was observed.

TABLE 21

Slurry Components and % by Wt. of Total Mixture for Treatment II** for Bunch and Runner Types

| | |
|---|---|
| Oil | 40.33 |
| Solids | 23.42 |
| Water | 32.54 |
| Emulsifiers Dyes & Additives | 3.71 |
| Total % | 100.00 |

EXAMPLE 12

BUNCH & RUNNER TYPE PEANUTS

A Treatment III slurry suspension (oil based) was prepared of this invention by blending together 3.0 fl. oz. of 42-S (Thiram); 3.0 fl. oz. Botran 30C; 3.0 fl. oz. Vitavax 30C; 6.0 fl. oz. Gustafson Peanut Binder; 2 cc of Rhodamine dye; 2 cc of Triton B-1956. This suspension was blended adequately to obtain a homogenous mixture and then was applied at a rate of 4.4 cc per pound. On the lab test, the germination and the % disease control were equivalent to the dust standard.

TABLE 22

Slurry Components and % by Wt. of Total Mixture for Treatment III for Bunch and Runner Types

| | III |
|---|---|
| Oil | 33.13 |
| Solids | 30.63 |
| Water | 33.41 |
| Emulsifiers & Dyes | 2.83 |
| Total % | 100.00 |

EXAMPLE 13

SPANISH & VALENCIA TYPE PEANUTS

A Treatment II oil suspension (oil based) was prepared of this invention by blending together 3.0 fl. oz. of 42-S (Thiram); 3.0 fl. oz. Botran 30C; 6.0 fl. oz. Gustafson Peanut Binder; 4 cc of Rhodamine dye; 4 cc of Triton B-1956. This suspension was blended adequately to obtain a homogeneous mixture and then was applied at a rate of 3.6 cc per pound. Twenty Thousand pounds of seed were commercially treated and 200 acres planted. Field performance was excellent with no planter plate build up.

TABLE 23

Slurry Components and % by Wt. of Total Mixture for Treatment II for Spanish & Valencia Types

| | II |
|---|---|
| Oil | 36.08 |
| Solids | 33.45 |
| Water | 26.95 |
| Emulsifiers & Dyes | 3.52 |
| Total % | 100.00 |

EXAMPLE 14

SPANISH & VALENCIA TYPE PEANUTS

A Treatment III slurry suspension (oil based) was prepared of this invention by blending together 3.0 fl. oz. of 42-S (Thiram); 3.0 fl. oz. of Botran 30C; 3.0 fl. oz. Vitavax 30C; 3.0 fl. oz. of Gustafson Peanut Binder; 4 cc of Rhodamine Dye; 4 cc of Triton B-1956. This suspension was blended to obtain a homogenous mixture and then applied at a rate of 3.6 cc per pound. Ten thousand pounds were treated commercially and 100 acres planted. Field and laboratory results were excellent.

TABLE 24

Slurry Components and % by Wt. of Total Mixture for Treatment III for Spanish & Valencia Types

| | III |
|---|---|
| Oil | 27.38 |
| Solids | 34.11 |
| Water | 35.29 |
| Emulsifiers | 3.22 |
| Total % | 100.00 |

It will be seen that applying seed treatments in the form of an oil based slurry or suspension containing the active contact type chemicals at rates of six to sixteen ounces of total treatment per hundred weight of peanut seed provides effective protection against the pathogens which are of primary concern in the planting and growing of peanuts.

What is claimed is:

1. Treated peanut seeds comprising peanut seeds with the testa intact on the cotyledons, and a coating for treating the seeds applied onto the testa, the coating being produced by treating the seeds with a colloidal suspension including oil as a base and also including micronized seed treating active chemicals carried by the oil in the suspension, the suspension being applied to the peanut seeds at a rate in the range of 6 to 16 fluid ounces per hundred weight of peanut seeds, and the seeds being allowed to dry with the result that the coating including active chemicals remains on the seeds whereby they minimize chemical dust related environmental and physical problems.

2. The treated peanut seeds according to claim 1 and the suspension also including emulsifier and a portion of water.

3. Peanut seeds having a treatment on peanut seeds with the testa intact on the cotyledon, the treatment being obtained by treating the testa of the peanut seeds with a colloidal suspension including oil as a base and also including micronized, seed treating active chemicals carried by the oil base in the suspension, said suspension being applied at a rate in the range of 6 to 16 fluid ounces per hundred weight of said peanut seeds, and allowing the seeds to dry with the result that coating including active chemicals remains on the seeds whereby to minimize dust related environmental and physical problems.

4. Treated peanut seeds comprising peanut seeds with their testae intact on the cotyledons and having a dried treatment coating on the testae applied as a liquid slurry including a balance of non-phytotoxic mineral oil as a base, water, emulsifier, and solid materials including micronized, seed treating active chemicals, the liquid slurry being applied to the peanut seeds at a rate in the range of 6 to 16 fluid ounces per hundred weight of peanut seeds.

5. The treated seeds according to claim 4 wherein the proportion of oil in the slurry is between twenty five and forty five percent by weight of the slurry.

6. The treated seeds according to claim 4 wherein the proportion of water in the slurry is up to thirty eight percent by weight of the slurry.

7. The treated seeds according to claim 4 wherein the proportion of oil is between twenty five and forty five percent by weight of the slurry, and the proportion of water is up to thirty eight percent by weight of the slurry.

* * * * *